United States Patent
Renimel et al.

(10) Patent No.: US 8,697,153 B2
(45) Date of Patent: Apr. 15, 2014

(54) **EXTRACT OF THE PLANT *RAVENALA MADAGASCARIENSIS* AND USE AS COSMETIC HYDRATING AGENT**

(75) Inventors: Isabelle Renimel, Trainou (FR); Patrice Andre, Neuville aux Bois (FR)

(73) Assignee: LVMH Recherche, Saint Jean de Braye (FR)

( * ) Notice: Subject to any disclaimer, the term of this patent is extended or adjusted under 35 U.S.C. 154(b) by 54 days.

(21) Appl. No.: 12/967,560

(22) Filed: Dec. 14, 2010

(65) Prior Publication Data

US 2011/0159097 A1 Jun. 30, 2011

(30) Foreign Application Priority Data

Dec. 29, 2009 (FR) ...................................... 09 59651

(51) Int. Cl.
*A61K 36/00* (2006.01)
(52) U.S. Cl.
USPC ........................................... 424/774; 424/725
(58) Field of Classification Search
None
See application file for complete search history.

(56) References Cited

U.S. PATENT DOCUMENTS

2007/0191666 A1* 8/2007 Watanabe et al. ............. 588/249
2011/0223121 A1* 9/2011 Andre et al. ................... 424/61

FOREIGN PATENT DOCUMENTS

| FR | 2 001 504 A1 | 6/2001 |
| FR | 2 930 557 | 4/2008 |
| WO | WO 2007/007255 A2 | 1/2007 |
| WO | WO 2009/138697 A1 | 11/2009 |

OTHER PUBLICATIONS

Itani et al. J. Weed Sci. Technol. 1999. vol. 44, No. 4, pp. 316-323, CROPU Abstract enclosed.*
Sougrat et al., "Functional Expression of AQP3 in human epidermis and keratinocyte cell cultures," *J. Invest. Dermatol.* (2002) 118: 678-685.
Snyder et al., "Classification of the solvent properties of common liquids," *Journal of Chromatography* (1974) 92: 223-230.
Jung et al., "Molecular structure of the water channel through aquaporin CHIP," *The Journal of Biological Chemistry* (1994) 269 (20): 14648-14654.
Ramiarantsoa et al., "Le O-β-D-glucoside du β-sitosterol Isole des Feuilles de *Ravenala madagascariensis*," *J. Soc. Ouest-Afr. Chim* (2008) 026: 99-103. English Abstract Included. XP007914489.
Jain et al., "Traditional uses of some Indian plants among islanders of the Indian Ocean," *Indian Journal of Traditional Knowledge, Resources* (2005) 4 (4): 345-357. XP01021348.
Search Report for priority French application FR 0959651, mailed Aug. 20, 2010.

* cited by examiner

*Primary Examiner* — Chris R Tate
(74) *Attorney, Agent, or Firm* — Merchant & Gould P.C.

(57) ABSTRACT

An extract is from the plant *Ravenala madagascariensis*. The sap from the plant *Ravenala madagascariensis* or of an extract of that plant is used as a hydrating active agent in a cosmetic composition, to restore, maintain or reinforce the hydration state of the skin.

15 Claims, No Drawings

EXTRACT OF THE PLANT *RAVENALA MADAGASCARIENSIS* AND USE AS COSMETIC HYDRATING AGENT

This application claims the benefit of Serial No. 0959651, filed Dec. 29, 2009 in France and which application is incorporated herein by reference. A claim of priority to which, to the extent appropriate, is made.

BACKGROUND OF THE INVENTION

The subject of the present invention is a novel extract of the plant *Ravenala madagascariensis*, and the use thereof as a cosmetic active agent to restore, maintain or reinforce the hydration state of the skin, a cosmetic composition containing it, and cosmetic care methods using said composition.

The plant *Ravenala madagascariensis* is a tree endemic to Madagascar which belongs to the family of the Strelitziaceae. It is currently regarded as the only species, *Ravenala madagascariensis* Sonn., of a monospecific genus. This tree is remarkable for the arrangement of its leaves in a fan shape. It is better known under the name of "the traveller's tree". English speakers refer to it as "traveller's tree" or else as "traveller's palm" although it is not a palm tree. Also present in other countries, in particular in Surinam, it is easily cultivated in tropical countries, in particular as an ornamental tree.

PRIOR ART

The maintenance of the hydration state of the skin is a major problem of the cosmetics industry, which is looking for hydrating cosmetic agents usable in any type of cosmetic composition, and also new targets on which these active agents can act, in particular to limit the evaporation of water or improve the transport of water within the epidermis.

The aquaporins (AQP) are a family of transmembrane proteins forming channels which facilitate the diffusion of water and small molecules, such as glycerol and urea, in solution.

The size of these aquaporins is about 30 kDa with 6 alpha helix transmembrane crossings (Jung et al., *J. Biol. Chem.* 1994, 269 (20), 14648-54).

They are widely distributed in the body and quite particularly in the organs which are the site of substantial movements of water between different compartments, such as the kidney (reabsorption of water) or the skin (transepidermal water loss).

AQP-3, demonstrated in the plasma membrane of the keratinocytes of the human epidermis, is distributed throughout the live epidermis (R Sougrat et al., *JID* 2002, 118: 678-685 and *Molec. Biol. Cell.;* 1998; vol. 9, 499a).

FR 2801504 discloses an extract of *Ajuga turkestanica* as an agent stimulating the expression of AQP3 and the use thereof in cosmetics as a hydrating agent.

WO 2007/007255 discloses various agents stimulating the expression of aquaporins AQP3 and AQP9 in the skin, as well as the use thereof in cosmetics.

It is moreover well known that certain substances, among them dexamethasone, stimulate the expression of aquaporins, in particular that of the AQP-3.

However, no document discloses the hydrating properties of an extract according to the invention, by stimulation of the expression of AQP3 in the cells of the epidermis.

This property renders particularly interesting the use of such an extract in cosmetic compositions to provide care whose aim is to maintain or favour the hydration of the skin.

SUMMARY OF THE INVENTION

The principal purpose of the invention is to provide a novel hydrating agent of the skin, in particular to restore, maintain or reinforce the hydration state of the skin.

A further main purpose of the invention is to provide a cosmetic composition containing such a hydrating agent.

Also a main purpose of the present invention is to provide a cosmetic care method using said cosmetic composition, in particular to restore, maintain or reinforce the hydration state of the skin.

Finally, a main purpose of the invention is to provide a simple solution, usable on the industrial and cosmetic scale.

DETAILED DESCRIPTION OF THE INVENTION

According to a first aspect, the invention relates to a plant extract obtained from sap from the plant *Ravenala madagascariensis* or from a plant material containing or formed by plant tissues rich in sap from said plant, such as the young leaves.

The harvesting of sap is performed under conditions making it possible to minimize bacterial contamination.

Once harvested, the sap is advantageously dried by any method known to those skilled in the art, for example heated by means of a rotary evaporator of the Rotavapor® type.

The plant tissues rich in sap constitute a preferred plant material for the implementation of an extraction process for the preparation of a plant extract according to the invention, possibly followed by a stage aiming to purify and isolate these compounds.

These tissues rich in sap are in particular the young leaves of *Ravenala madagascariensis*.

In the early stages of its development, the leaf first grows rolled around its central median vein. It then unrolls, but without tearing at the transverse veins. At these stages, it is of a light green colour. At these early stages of development, the leaf is still strongly impregnated with sap.

Thus, in the sense of the present invention, the expressions "young leaf" or "immature leaf" correspond to the early stages of development of the leaves described above. Preferably, the young leaves used as plant material for preparing the extracts according to the present invention are aged less than about forty-five days and preferably less than thirty days.

Unlike a young leaf, a leaf of *Ravenala madagascariensis* at a mature stage is easily recognizable by the many tears along the transverse and dry veins of the leaf.

The extract according to the invention is more particularly obtained by treatment of the sap or of young leaves constituting a plant material rich in sap, by means of a polar solvent or a mixture of polar solvents.

According to the present invention, the expression "polar solvent" signifies that the solvent has a polarity index value P' which is greater than or equal to a value of 4. The polarity index is a quantity calculated on the basis of thermodynamic quantities (solubility and change of state) which indicates the more or less polar character of a molecule. For the polarity indices of solvents, reference will be made to the article by L. R. SNYDER (*J. chromatogr.,* 92 (1974), 223-230, which is included in the present application by reference.

The polar solvent, or the polar solvents forming a mixture, are advantageously selected from water, a $C_1$-$C_4$ alcohol, in particular ethanol or butanol, or else a glycol, in particular glycerol, butylene glycol or propylene glycol.

A preferred extract is more particularly obtained by treatment with water or an aqueous alcohol mixture such as a mixture of water and ethanol.

A preferred extract is more particularly obtained by treatment with a mixture of ethanol and water in a 70/30 ratio (V/V).

Thus, a second subject of the invention relates to the use in a cosmetic composition of the sap from the plant *Ravenala madagascariensis* or of an extract as previously defined, as a hydrating agent to restore, maintain or reinforce the hydration state of the skin.

According to the invention, the sap or the extract as previously defined is present as an active agent in a cosmetic composition, in an effective quantity for obtaining the desired effect on topical application.

The expression "effective quantity", is understood to mean a quantity of sap or of extract which makes it possible to obtain the desired effect, in the present case an action on the hydration of the skin.

According to a third aspect, the invention relates to a cosmetic composition characterized in that it contains as an active agent the sap from the plant *Ravenala madagascariensis* or an extract as previously defined.

According to a preferred implementation, the cosmetic composition contains as an active agent an extract of young leaves of the plant *Ravenala madagascariensis* as previously described and more particularly obtained by means of a polar solvent or a mixture of polar solvents.

According to particular implementation mode of the invention, the cosmetic composition contains from 0.001% to 2%, preferably from 0.01% to 0.2%, in dry weight of the sap from the plant *Ravenala madagascariensis* or of an extract as previously defined.

The cosmetic composition according to the invention can also contain one or more other molecules or plant extracts exhibiting hydrating properties, such as glycerol, or natural polyols, natural or synthetic ceramides, urea, hyaluronic acid, or else also an extract of *Ajuga turkestanica*, an extract of *Vanda coerulea*, retinoic acid, D-xylose, an extract of *Malva sylvestris* or an extract of *Centella asiatica*.

These molecules or extracts, which also exhibit a skin hydrating effect, can thus play a part complementary to that of the active agents of the invention.

The cosmetic composition can further also contain one or more other cosmetic active agents selected from the group of substances having an anti-ageing activity, substances having a depigmenting activity or a skin lightening activity, substances having a slimming activity, substances having a hydrating activity, substances having a calming, soothing or relaxing activity, substances having an activity stimulating the cutaneous microcirculation to improve the bloom of the complexion, in particular of the face, substances having a sebum regulating activity for the care of greasy skins, substances intended to clean or purify the skin and substances having an anti-free-radical activity.

In particular, the cosmetic composition can contain one or more other cosmetic active agents selected from:

agents stimulating the epidermal kallikreins which regulate the desquamation at the surface of the skin, in particular an extract of nopal, agents which stimulate the synthesis of the lipids of the epidermis and play an essential part in the water barrier effect of the stratum corneum and the suppleness of the skin, in particular an extract of seeds of *Helianthus annuus* L. or of *Luffa cylindrica*, agents which stimulate the terminal differentiation of the keratinocytes or transglutaminase, to reinforce the formation of the corneocytes and the cutaneous barrier, in particular beta-ecdysone or calcium derivatives such as calcium gluconate or calcium pyrrolidone carboxylate or else active agents stimulating the renewal of the epidermis in particular wheat oil, agents which favour the formation of tight junctions and thus limit intercellular losses of water, in particular an extract of *Castanea sativa* or the *Sanchi* saponins.

agents stimulating the synthesis of the glycosaminoglycans (GAG) at the epidermal level, such as D-xylose or a derivative of xylose, in particular a C-glycoside and derivatives thereof.

agents favouring cell renewal such as vitamin A (retinol) and/or esters thereof, in particular a propionate of vitamin A, alpha- or beta-hydroxy acids such as the fruit acids, malic acid, glycolic or citric acid, salicylic acid or esters thereof, gentisic acid or esters thereof in particular, tocopherol gentisate;

agents stimulating the firmness of the skin, such as peptides stimulating the synthesis of collagen, in particular type I, II, IV or VII collagen, an extract of *Centella asiatica*, madecassic acid, asiatic acid, madecassoside, an extract of oats, an extract of *Bertholletia exscelsa*, a hydrolysate of proteins, soya peptides, an extract of *Potentilla erecta*, an extract of *Siegesbeckia orientalis*, ginsenosides or notoginsenosides in particular Rb1 or R0;

agents regulating the differentiation of the epidermis, among them those of the ecdysteroid type, ecdysterone, turkesterone or calcium derivatives or precursors of vitamin D;

adenosine, carnitine or derivatives thereof;

inhibitors of metalloproteinases, in particular inhibitors of MMP1, MMP2, or MMP9 such as an extract of *Ruscus asculeatus* or *Annogeisus leicarpus* or flavonoids such as quercetin, kaempferol, apigenin, wogonin, or plant extracts containing them;

elastase inhibitors such as extracts of *Aspergillus fumigatus, Momordica charantia* or *Cucurbita maxima;* agents stimulating the synthesis of dermatopontin, such as an extract of amber;

agents tightening the pores such as extracts of astringent plants, for example an extract of witch hazel;

filters protecting from UVA and UVB radiation, such as benzophenone, 4-butyl methoxydibenzoylmethane, octocrylene, ethylhexyl methoxycinnamate, ethylhexyl salicylate, phenylbenzymidazole sulphonic acid, or homosalate, alone or in combination with oxides of titanium;

agents intended to combat pigmentation disorders, in particular those connected with ageing of the skin, such as kojic acid, extracts of liquorice or mulberry root, arbutin, calcium pantotheno-sulphonate, boldine, diacetyl-boldine, vitamin C and derivatives thereof, in particular glycosides, extracts of lily, in particular of the corm;

anti-free radical or anti-inflammatory agents such as an extract of *Artemisia capillaris*, an extract of *Sanguisorba officinalis*, resveratrol and derivatives thereof, *curcuma* or curcumin or tetrahydrocurcumin, polyphenols extracted from grape seeds, vitamin E and derivatives thereof, in particular phosphate derivatives thereof, ergothioneine or derivatives thereof or idebenone;

agents favouring the synthesis of hyaluronic acid at the epidermal and dermal level, or of glycosaminoglycans to give a hydrated and plump skin, in particular an extract of *Eriobotrya japonica* or fragments of hyaluronic acid of low molecular weight or else an extract of *Adenum obsesum*.

magnesium aspartate to improve the anti-wrinkle action and any one of the mixtures thereof.

Apart from at least one active agent, the cosmetic composition also contains at least one cosmetically acceptable excipient, useful for the preparation of said composition.

Advantageously, the composition further contains at least one cosmetically acceptable excipient which can be selected from pigments, dyes, polymers, surfactants, rheological agents, perfumes, electrolytes, pH adjusters, anti-oxidant agents, preservatives, and mixtures thereof.

The cosmetic composition can be in the form of a serum, a lotion, a cream or else also a hydrogel, and preferably a mask or else in the form of a stick or a patch.

Finally, a subject of the invention, according to a fourth aspect, is a cosmetic care method characterized in that it comprises the application onto at least one relevant zone of the skin of the face or the body, of sap or of an extract of young leaves of the plant *Ravenala madagascariensis*, or of a cosmetic composition containing as an active agent the sap from the plant *Ravenala madagascariensis* or a plant extract containing it as previously defined, to restore, maintain or reinforce the hydration state of the skin and/or for obtaining an effect of prevention or slowing of the appearance of the signs of skin dryness.

In the examples, all the percentages are given in weight, the temperature is in degrees Celsius, and the pressure is atmospheric pressure, unless otherwise indicated.

Other purposes, characteristics and advantages of the invention will appear clearly from the explanatory description which is to follow, made with reference to several implementation examples of the invention given simply for illustration and which are not intended in any way to limit the scope of the invention. In the examples, the temperature is in degrees Celsius, the pressure is atmospheric pressure and the quantities or percentages are given by weight, unless otherwise indicated.

EXAMPLES OF THE INVENTION

Example 1

Preparation of an Extract According to the Invention

The sap is extracted from *Ravenala madagascariensis* while as far as possible avoiding bacterial contamination of the sample, as is easily comprehensible to those skilled in the art. The sap is dried with a rotary evaporator, then taken up in a mixture of ethanol and water in a 70/30 volume/volume ratio. The solvent is then evaporated to dryness.

For the experiments of Example 4, an aqueous solution of the sap extract, with 5% by weight of dry extract, is prepared.

Example 2 According to the Invention

Preparation of an Extract of Young Leaves of *Ravenala madagascariensis*

Young leaves of *Ravenala madagascariensis*, aged three weeks at most, are harvested, dried and crushed. The plant material is extracted with a mixture of ethanol and water in a 70/30 volume/volume ratio. The solvent is evaporated to dryness.

Pour the experiments of Example 4, a solution of the aqueous alcoholic extract of young leaves, with 4% by weight of dry extract in DMSO, is prepared.

Example 3

Preparation of an Extract of Mature Leaves of *Ravenala madagascariensis*

Mature leaves of *Ravenala madagascariensis* are harvested, dried and crushed. The plant material is extracted with a mixture of ethanol and water in a volume/volume ratio of 70/30. Finally, the solvent is evaporated to dryness.

For the experiments of Example 4, a solution of the aqueous alcoholic extract of mature leaves, thus prepared, with 4% by weight of dry extract in DMSO, is prepared.

Example 4

Histological Analysis of Human Skin to Determine the Hydrating Activity of the Active Agents Tested Material and Method
Preparation of Biopsies
33 skin explants of about 10 mm diameter are prepared from an abdominal plasty on a 27 year-old woman. They are kept alive in a suitable medium.

Thirty explants are divided into 5 lots of 6 explants, and the three remaining explants will be used as untreated controls (lot: T0).
Treatment of Lots:

$1^{st}$ lot: 6 explants onto which is applied the excipient, which is an oil-in-water emulsion without the active agent tested.

$2^{nd}$ lot: 6 explants onto which is applied the same emulsion as before, and which further contains 4% by weight of the solution of Example 1, that is a final concentration in the emulsion of 0.2% by weight of dry extract of sap from *Ravenala madagascariensis*.

$3^{rd}$ lot: 6 explants onto which is applied the emulsion, which further contains 5% by weight of the solution of Example 2, that is a final concentration in the emulsion of 0.2% by weight of dry extract of young leaves of *Ravenala madagascariensis*.

$4^{th}$ lot: 6 explants onto which is applied the emulsion, which further contains 5% by weight of the solution of Example 3, that is a final concentration in the emulsion of 0.2% by weight of dry extract of mature leaves of *Ravenala madagascariensis*.

$5^{th}$ lot: 6 explants for the positive control: dexamethasone
The products are applied topically at the dosage of 2 mg per explant and spread with a small spatula.

The treatment is repeated for four successive days.
Samples and Histology
Samples The explants are sampled for histology over 4 days, on days D0, D1 and D4.

The 3 control explants of the T0 lot are sampled on day D0. Concerning the other 5 lots, 3 explants of each lot are sampled on day D1 and the other 3 on day D4.

Each explant is immediately cut into two. One half is fixed in buffered formalin and the other half is frozen at −80° C.
Histology After 24 hours of fixing in the buffered formalin, the samples are dehydrated and impregnated in paraffin using a Leica 1020 automatic dehydrator. They are incorporated into blocks using a Leica EG 1160 embedding station.

5 nanometer sections are made using a Leica RM 2125 Minot type microtome, and glued onto superfrost silanized glass histology slides.

The frozen samples are cut to 7 nm in a Leica CM 3050 cryostat. The sections are glued onto superfrost silanized glass histology slides for immunological labelling.

The microscope observations are made by optical microscopy, using a Leica DMLB type microscope, with ×40 objective lens. The micro-graphs are taken with a tri CCD Sony DXC 390P camera and stored using the Leica IM1000 data archiving software.

General Morphology

The observation of the general morphology is carried out on paraffin sections dyed with Masson trichrome. They are observed under optical microscopy.

Labelling of Aauaporins 3 (AQP3)

The explant sections embedded in paraffin are fixed with Bouin liquid (formalin+picric acid). The AQP3 is then labelled with a rabbit polyclonal anti-AQP3 antibody, available from Chemicon (ref AB 3276), then immunohistochemically developed with DAB (diaminobenzidine), giving rise to a chestnut colour.

Results

The results of the observations on the various sections of explants of Lots No. 1 to No. 5, at time D1 then at time D4, are discussed below and presented together in Table 1 below.

1—Labelling of Aquaporin-3 on D1

On the Untreated Explants (Lot No. 1):

The labelling is quite clear, definitely on the membranes. It is also more clearly displayed in the upper layers of the epidermis, with the exception of the last cell layer under the stratum corneum. It is very moderately displayed in the basal layers and is very little displayed on the basal pole of the basal keratinocytes.

On the Explants Treated with Dexamethasone (Positive Control) (Lot No. 5):

The labelling is quite clear, definitely on the membranes. It is also more clearly displayed in the upper layers of the epidermis. It is moderately present in the last cell layer under the stratum corneum. It is moderately displayed in the basal layers, above all in the basolateral spaces. It is very little displayed on the basal pole of the basal keratinocytes.

On the Explants Treated with the Formulation Containing the Sap from *Ravenala madagascariensis* (Lot No. 2):

The labelling is quite clear, definitely on the membranes. It is also more clearly displayed in the upper layers of the epidermis. It is slightly present in the last cell layer under the stratum corneum. It is moderately displayed in the basal layers, more clearly in the basolateral spaces. It is very little displayed on the basal pole of the basal keratinocytes.

On the Explants Treated with the Formulation Containing the Extract of Young Leaves of *Ravenala madagascariensis* (Lot No. 3):

The labelling is quite clear, definitely on the membranes. It is also clearly displayed in the upper layers of the epidermis. It is moderately present in the last cell layer under the stratum corneum. It is quite clearly displayed in the basal layers, above all in the basolateral spaces. It is moderately displayed on the basal pole of the basal keratinocytes.

On the Explants Treated with the Formulation Containing the Extract of Mature Leaves of *Ravenala madagascariensis* (Lot No. 4):

The labelling is not very clear and is very little displayed in the upper epidermal layers. It is moderately present in the last cell layer under the stratum corneum. It is little displayed in the basal layers, more clearly in the basolateral spaces. It is very little displayed on the basal pole of the basal keratinocytes.

2—Labelling of AQP-3 on D4

On the Untreated Explants (Lot No. 1):

The labelling is quite clear, definitely on the membranes, and is slightly more displayed in the upper epidermal layers. It is not present in the last cell layer under the stratum corneum. It is very moderately displayed in the basal layers, above all in the basolateral spaces. It is very little displayed on the basal pole of the basal keratinocytes.

On the Explants Treated with the Dexamethasone (Positive Control) (Lot No. 5):

The labelling is very clear, definitely on the membranes, and is clearly displayed in the upper epidermal layers. It is slightly present in the last cell layer under the stratum corneum. It is very clearly displayed in the basal layers, above all in the basolateral spaces. It is very little displayed on the basal pole of the basal keratinocytes.

On the Explants Treated with the Formulation Containing the Sap from *Ravenala madagascariensis* (Lot No. 2):

The labelling is clear, definitely on the membranes, and is very clearly more displayed in the upper epidermal layers. It is quite clearly present in the last cell layer under the stratum corneum. It is clearly displayed in the basal layers, above all in the basolateral spaces. It is moderately displayed on the basal pole of the basal keratinocytes.

On the Explants Treated with the Formulation Containing the Extract of Young Leaves of *Ravenala madagascariensis* (Lot No. 3):

The labelling is very clear, definitely on the membranes and is clearly displayed in the upper epidermal layers. It is moderately present in the last cell layer under the stratum corneum. It is quite clearly displayed in the basal layers, above all in the basolateral spaces. It is moderately displayed on the basal pole of the basal keratinocytes.

On the Explants Treated with the Formulation Containing the Extract of Mature Leaves of *Ravenala madagascariensis* (Lot No. 4):

The labelling is not very clear and is very little displayed in the upper epidermal layers. It is moderately present in the last cell layer under the stratum corneum. It is little displayed in the basal layers, more clearly in the basolateral spaces. It is very little displayed on the basal pole of the basal keratinocytes.

TABLE 1

Labelling of the AQP3s on D1 and D4 based on the layers of the epidermis

| Lot | | Membrane labelling | | Upper layers | | Last cell layer under the stratum corneum | | Basal layers | | Basal pole of the basal keratinocytes | |
|---|---|---|---|---|---|---|---|---|---|---|---|
| No. | Treatment | D1 | D4 | D1 | D4 | D1 | D4 | D1 | D4 | D1 | D4 |
| No. 1 | Untreated (excipient) | XXX | XXX | XXXX | XXX | 0 | 0 | XX | XX | X | X |

TABLE 1-continued

Labelling of the AQP3s on D1 and D4 based on the layers of the epidermis

| Lot No. | Treatment | Membrane labelling | | Upper layers | | Last cell layer under the stratum corneum | | Basal layers | | Basal pole of the basal keratinocytes | |
|---|---|---|---|---|---|---|---|---|---|---|---|
| | | D1 | D4 | D1 | D4 | D1 | D4 | D1 | D4 | D1 | D4 |
| No. 5 | Dexamethasone (positive control) | XXXXX | XXXXX | XXXXX | XXXXX | XXX | XX | XXX | XXXXX | X | X |
| No. 2 | Sap | XXX | XXXX | XXXX | XXXXX | XXX | XXX | XXX | XXXX | X | XXX |
| No. 3 | Extract of young leaves | XXXXX | XXXXX | XXXX | XXX | XXX | XXX | XXXX | XXX | XXX | XXX |
| No. 4 | Extract of mature leaves | XX | X | X | X | XXX | XXX | XXX | XX | X | X |

Key to table:
Labelling very clearly displayed: XXXXX
Labelling clearly displayed: XXXX
Labelling quite clearly displayed or moderately displayed: XXX
Labelling very moderately displayed: XX
Labelling very little displayed: X
No labelling: 0

CONCLUSIONS

The extract of sap and the aqueous alcoholic extract of young leaves of Ravenala madagascariensis both exhibit particularly interesting cosmetic properties. These extracts have particular efficacy for regulating the water flows in the epidermis. The labelling of the AQP-3 makes it possible to demonstrate a remarkable activity of the active agents tested on the regulation and/or the functionality of the AQP3 aquaporins. This activity results in better hydration of the basal layers of the epidermis.

The invention claimed is:

1. A skin care cosmetic composition containing, as an active agent, from 0.001% to 2%, in dry weight, of
a hydroalcoholic extract obtained from young leaves aged less than about forty-five days of the plant Ravenala madagascariensis, wherein said extract is an active agent that restores, maintains or reinforces the hydration state of the skin and/or obtains an effect of prevention or retardation of the appearance of the signs of skin dryness.

2. The cosmetic composition according to claim 1 wherein the composition further contains at least one ingredient selected from the group consisting of plant extracts exhibiting hydrating properties, glycerol, natural polyols, natural or synthetic ceramides, urea, hyaluronic acid, an extract of Ajuga turkestanica, an extract of Vanda coerulea, retinoic acid, D-xylose, an extract of Malva sylvestris, and an extract of Centella asiatica.

3. The composition according to claim 1 wherein the composition further contains at least one cosmetically acceptable excipient selected from the group consisting of pigments, dyes, polymers, surfactants, rheological agents, perfumes, electrolytes, pH adjusters, antioxidant agents, and preservatives.

4. The composition according to claim 1 wherein the composition is in the form of a serum, a lotion, a cream, a hydrogel, a mask, a stick, or a patch.

5. The cosmetic composition according to claim 1, wherein the hydroalcoholic extract obtained from young leaves is obtained by treatment of the young leaves with a mixture of ethanol and water in a 70/30 ratio (v/v).

6. The cosmetic composition according to claim 1, wherein said extract is obtained by using a mixture of water and a $C_1$-$C_4$ alcohol.

7. The cosmetic composition according to claim 6 wherein the composition further contains at least one ingredient selected from the group consisting of plant extracts exhibiting hydrating properties, glycerol, natural polyols, natural or synthetic ceramides, urea, hyaluronic acid, an extract of Ajuga turkestanica, an extract of Vanda coerulea, retinoic acid, D-xylose, an extract of Malva sylvestris, and an extract of Centella asiatica.

8. The composition according to claim 6 wherein the composition further contains at least one cosmetically acceptable excipient selected from the group consisting of pigments, dyes, polymers, surfactants, rheological agents, perfumes, electrolytes, pH adjusters, antioxidant agents, and preservatives.

9. The composition according to claim 6 wherein the composition is in the form of a serum, a lotion, a cream, a hydrogel, a mask, a stick, or a patch.

10. The cosmetic composition according to claim 6, wherein said extract is obtained by using a mixture of water and a $C_1$-$C_4$ alcohol selected from the group consisting of ethanol and butanol.

11. The cosmetic composition according to claim 10 wherein the composition further contains at least one ingredient selected from the group consisting of plant extracts exhibiting hydrating properties, glycerol, natural polyols, natural or synthetic ceramides, urea, hyaluronic acid, an extract of Ajuga turkestanica, an extract of Vanda coerulea, retinoic acid, D-xylose, an extract of Malva sylvestris, and an extract of Centella asiatica.

12. The composition according to claim 10 wherein the composition further contains at least one cosmetically acceptable excipient selected from the group consisting of pigments, dyes, polymers, surfactants, rheological agents, perfumes, electrolytes, pH adjusters, antioxidant agents, and preservatives.

13. The composition according to claim 10 wherein the composition is in the form of a serum, a lotion, a cream, a hydrogel, a mask, a stick, or a patch.

14. A method of hydrating the skin of a subject in need thereof comprising:

applying an effective amount of the skin care cosmetic composition according to claim 1 to the skin of said subject.

15. A cosmetic skin care method comprising:

applying the skin care cosmetic composition according to claim 1 onto at least one zone of the skin of the face or the body of a subject in need thereof, wherein the composition is applied in an amount effective to restore, maintain or reinforce the hydration state of the skin and/or to obtain an effect of prevention or retardation of the appearance of the signs of skin dryness.

* * * * *